US00PP36308P2

(12) United States Plant Patent
Dirr et al.

(10) Patent No.: US PP36,308 P2
(45) Date of Patent: Dec. 10, 2024

(54) ***BAPTISIA* PLANT NAMED 'PIIBAP-01-21'**

(50) Latin Name: ***Baptisia* hybrid**
Varietal Denomination: PIIBAP-01-21

(71) Applicant: Premier Introductions, Inc., Watkinsville, GA (US)

(72) Inventors: Michael Dirr, Bogart, GA (US); Jeff Beasley, Lavonia, GA (US); Mark Griffin, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/635,741

(22) Filed: Apr. 15, 2024

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP26,587 P2 * 4/2016 Hansen ..... A01H 5/02
Plt./263.1

* cited by examiner

*Primary Examiner* — Karen M Redden
(74) *Attorney, Agent, or Firm* — Cassandra Bright

(57) ABSTRACT

A new and distinct cultivar of *Baptisia* plant named 'PIIBAP-01-21', characterized by its dusky purple stems, peduncles, and pedicels fading to green as they age, purplish-blue flowers with a hidden pale yellow-green keel, dark olive-green tri-foliate foliage, upright uniform, vase shaped plant habit, and produces abundant flowers and flower stems.

4 Drawing Sheets

Genus and species of plant claimed: *Baptisia* hybrid.
Variety denomination: 'PIIBAP-01-21'.

BACKGROUND OF THE INVENTION

The present invention relates to a new and distinct cultivar of hybrid *Baptisia*, hereinafter referred to by its cultivar name 'PIIBAP-01-21'. This cultivar is grown primarily as an herbaceous perennial for landscape and cut flowers. This cultivar originated from an open pollination of *Baptisia* x *variicolor* 'Twilite' (U.S. Plant Pat. No. 19,011) in Watkinsville, GA in 2019, and was selected from the progeny by continued evaluation for growth habit, floral, and foliage characteristics.

'PIIBAP-01-21' has been asexually reproduced by softwood cuttings since 2019 in Watkinsville, GA. The characteristics of the cultivar have been stable and reproduced true-to-type in successive vegetative generations.

SUMMARY OF THE INVENTION

'PIIBAP-01-21' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'PIIBAP-01-21' from all other varieties in commerce known to the Inventors. 1) Dusky-violet stems, petioles, stipules, peduncles, pedicels, and flower buds emerge, fading to green once the plant matures. 2) Purplish-blue flowers with a hidden pale yellow-green keel. 3) Dark olive-green tri-foliate foliage. 4) Upright uniform, vase shaped plant habit. 5) Produces abundant flowers and flower stems.

PARENTAL COMPARISON

'PIIBAP-01-21' is distinguished from its parent plant *Baptisia* x *variicolor* 'Twilite' (U.S. Plant Pat. No. 19,011) by the color of its new growth until the plant matures. 'PIIBAP-01-21' has dusky-violet stems, petioles, stipules, peduncles, pedicels and flower buds until the plant begins to age and they fade to green, but 'Twilite' emerges with green petioles, stipules, peduncles, pedicels and flower buds and remains green. 'PIIBAP-01-21' has a columnar habit becoming more vase-shape as foliage develops, where 'Twilite' has an upright plant habit. 'PIIBAP-01-21' has olive-green foliage and 'Twilite' has blue-green foliage.

COMMERCIAL COMPARISON

'PIIBAP-01-21' can be compared to the cultivar 'Purple Smoke' (unpatented). 'PIIBAP-01-21' has stems, petioles, stipules, peduncles, pedicels, and flower buds that emerge dusty violet until they mature and become olive green. 'Purple Smoke' emerges with charcoal grey stems and does not have the dusty violet color on the stems, petioles, stipules, peduncles, pedicels, and flower buds.

'PIIBAP-01-21' can be compared to the cultivar 'Grape Taffy' (U.S. Plant Pat. No. 26,587). 'PIIBAP-01-21' has purple-blue flowers and 'Grape Taffy' has violet flowers. 'PIIBAP-01-21' has stems, petioles, stipules, peduncles, pedicels, and flower buds that are a dusty violet color until maturity. 'Grape Taffy' stems, petioles, stipules, peduncles, pedicels, and flower buds emerge green.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Baptisia*.

Figure 1:
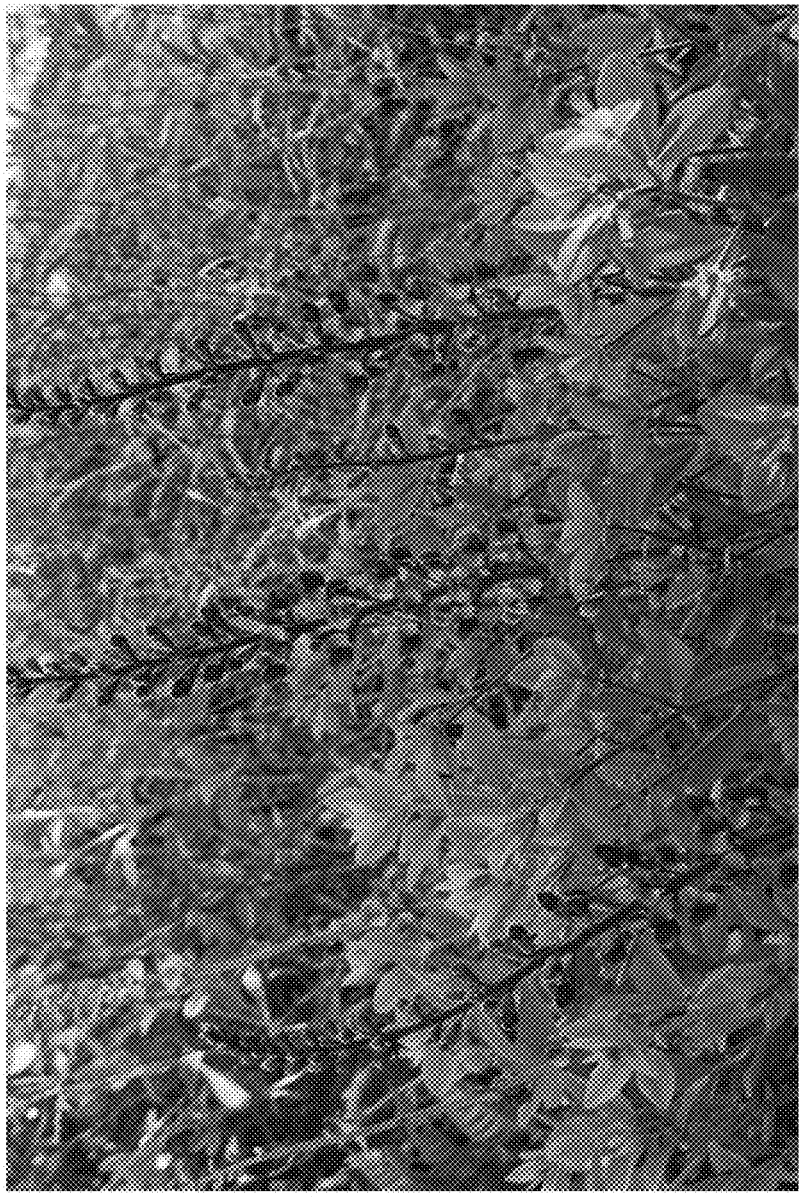
FIG. 1 shows a four-year-old 'PIIBAP-01-21', with flowers.
Figure 2:
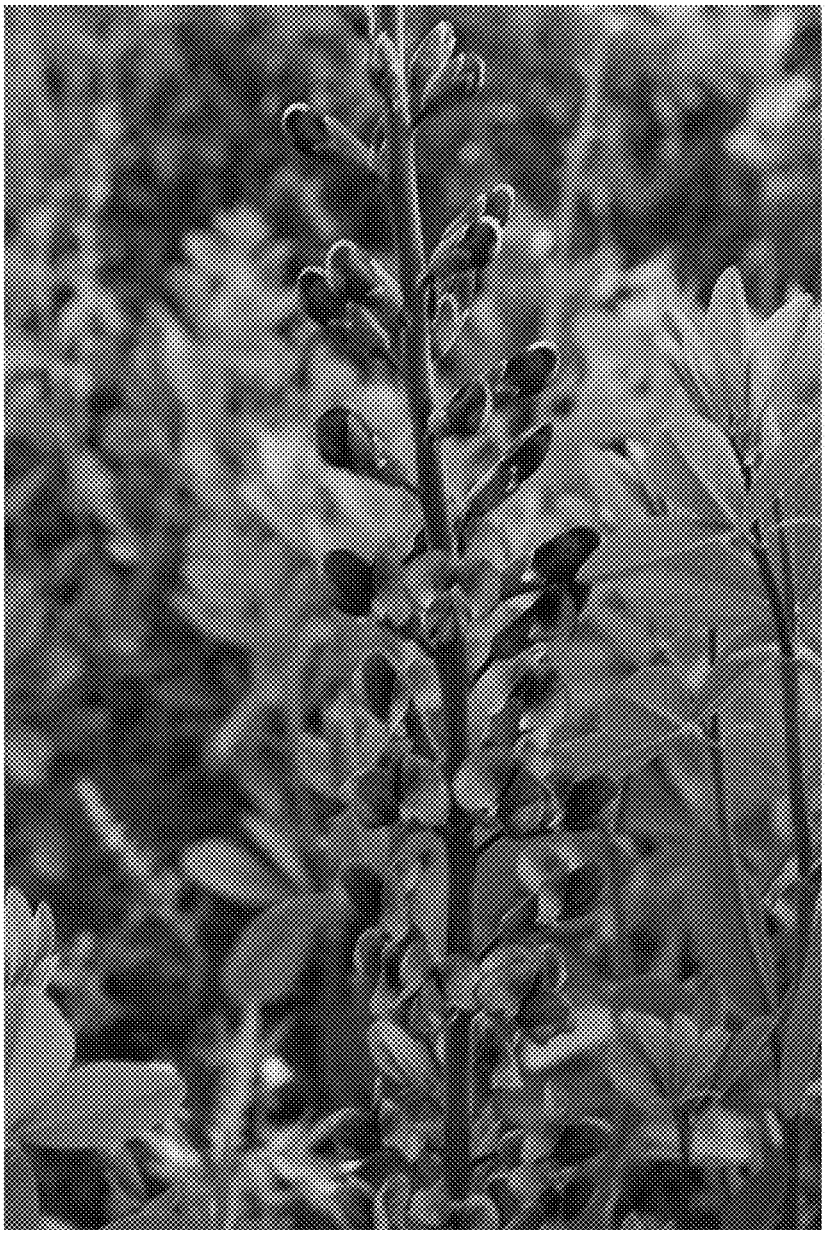
FIG. 2 shows a four-year-old 'PIIBAP-01-21' plant's flower stalk showing flowers and dusky purple stems, peduncles, and pedicles.
Figure 3:
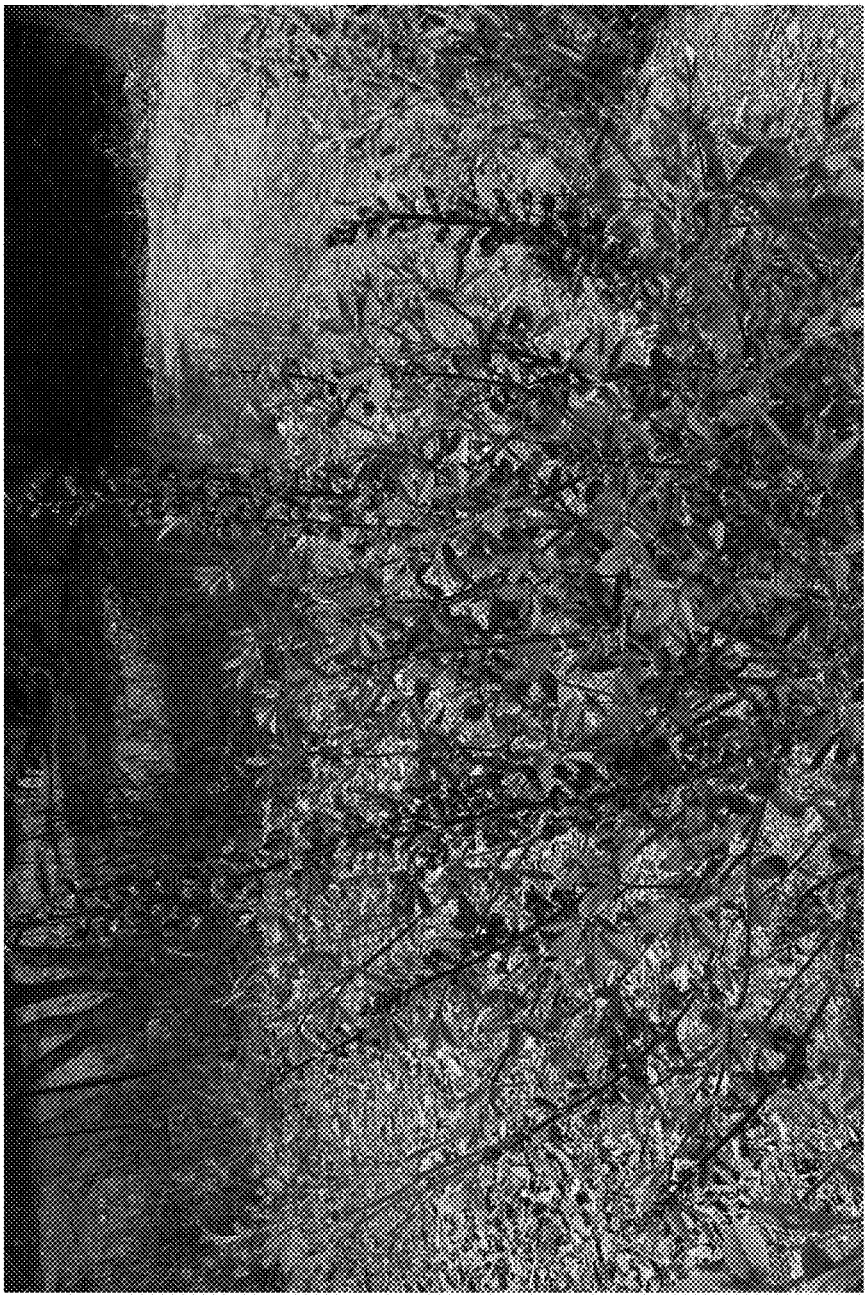
FIG. 3 shows a four-year-old 'PIIBAP-01-21' plant in the ground.
Figure 4:
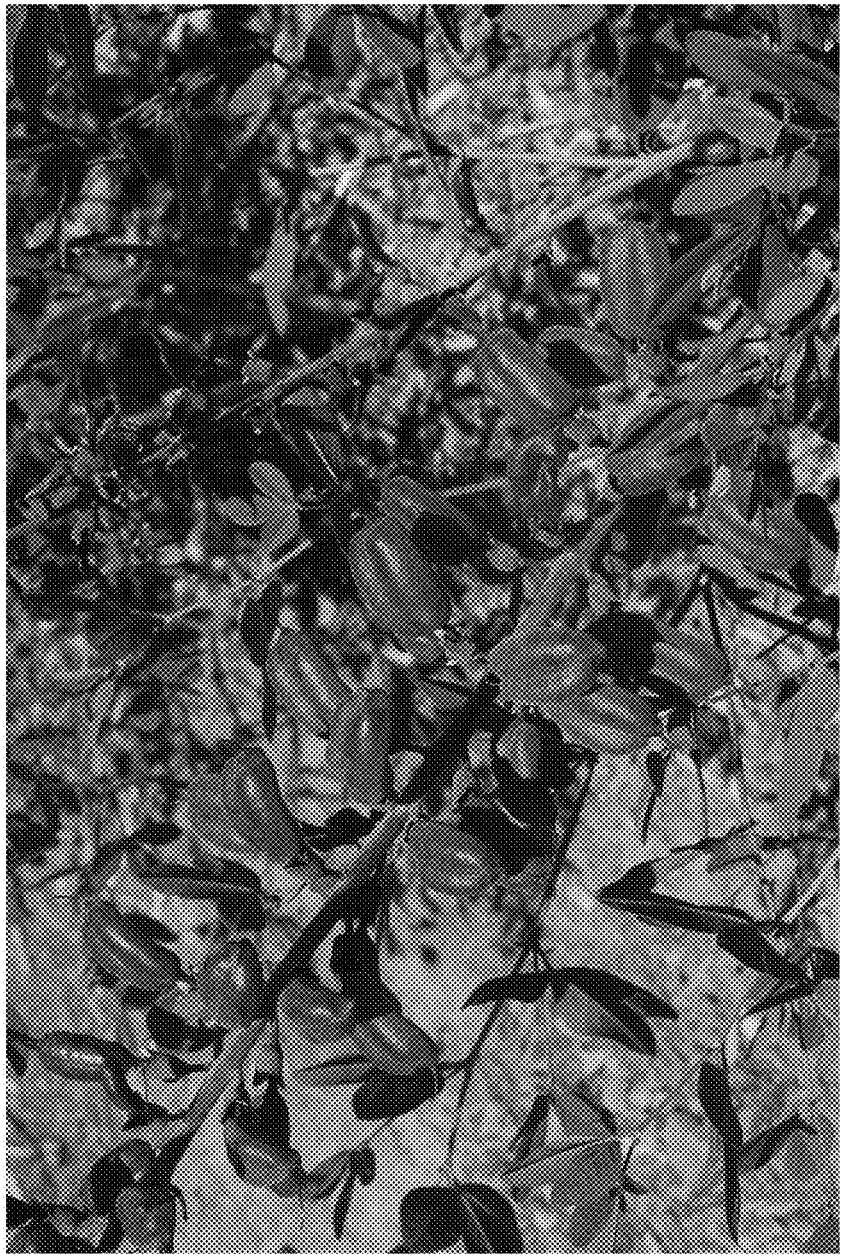
FIG. 4 shows a four-year-old 'PIIBAP-01-21' plant with fruit.

In the following description, color references are made to The Royal Horticultural Society Colour Chart, 2015 Edition, except where general terms of ordinary dictionary significance are used. Plants for the description were grown in 11.35 L containers in greenhouse conditions in a nursery in Watkinsville, GA. Plants were about four years old when the description was recorded.

Detailed description:

*Botanical classification.*—'PIIBAP-01-21' is a cultivar of a hybrid *Baptisia*. The current variety is a progeny from an open pollination of *Baptisia* x *variicolor* 'Twilite' (U.S. Plant Pat. No. 19,011) in Watkinsville GA in 2020. Propagation: Vegetatively by stem cuttings taking about 3 weeks.

Plant description:

*Plant habit.*—Perennial, upright, branched, vase-shaped growth habit with long inflorescence held in and above the foliage. The four-year-old plant in a container is 76 cm tall and 79 cm wide. Growth Rate: Fast, *Baptisia* emerge from the ground and are in flower in a month.

*Stem description.*—Branch habit: Densely branched; Primary branches 45° angle above horizontal; 12 branches with 5 secondary branches, and 4 tertiary branches. Stem size: 76 cm (including peduncle) in length and 6 mm in width; secondary: 24 cm in length and 3 mm in width; tertiary: 5 cm in length and 2 mm in width. Stem shape: Rounded. Stem color: emerges N92A, and as it matures it becomes 138B. Satiny, slightly glaucous. Internodes up to 5 cm apart, lowest branches internodes average about 10 cm.

*Roots.*—Deep rooted, thick, fleshy. Root Color: 162A.

Leaves:

*Foliage.*—Fan shaped. Leaf division: Ternate. Leaf internode: Foliage begins 10 cm from the base, 8 cm on main stem and 5 cm on secondary branches. Leaf size: 9 cm in length and 6 cm in width when mature. Leaf quantity: about 40 per stem. Leaflet shape: Emarginate. Leaflet base: Cuneate. Leaflet apex: Acute. Foliage Venation: Pinnate pattern, not conspicuous, about 6-8 veins per leaflet; color matches leaflet color on upper and lower surface with mid rib of lower surface 137D. Leaflet margins: entire. Leaf attachment: Petiolate. Leaf arrangement: alternate. Leaflet surface: Glabrous and slightly glaucous on upper and lower surface. Leaflet color: Newly expanding foliage 147A on upper and lower surface; on mature leaflets NN137A on upper and 137D lower surface. Leaflet size 4 cm in length and 2 cm in width.

*Petioles.*—2.5 cm in length and 2 mm in width, clasping to stem at mature nodes, 143A in color, surface is glabrous and satiny. Stipules: lanceolate in shape, base is cuneate to stem, apex is narrowly acute to acuminate, 2.5 cm in length and 6 mm in width on mature leaves, 138C in color on upper and lower surface.

Flowers:

*Flower description.*—Inflorescence type: Terminal racemes of papilionaceous flowers on main and secondary branches, open from base to the apex, acropetal development. Inflorescence size: 24.5 cm in length and 4 cm in width in mid-section. Persistence of inflorescence: approximately 20 days. Flower size: 2.6 cm in length and 1.7 cm in diameter. Flower number per inflorescence about 40 to 50.

*Flower fragrance.*—None detected.

*Peduncle.*—Round in shape, 32 cm in length and 5 mm in width, initially N92C with a coating of 191A in color, surface is glabrous, satiny and slightly glaucous, flower internode length 0.8 cm to 2 cm. Pedicel: 5 mm in length and 1 mm in width, round in shape (cross section), N92B with a tinting of 191A in color, glabrous and satiny surface. Flower buds: Kidney-shaped, 2.8 cm in length and 1 cm in width, 92B in color aging to 138B in color with residual N89A. Petal portion: Upper surface (adaxial) N92D and lower surface (abaxial) 94C in color.

*Flower type.*—Papilionaceous, bilaterally symmetrical, held at a 50-degree angle. Calyx: Campanulate, about 1 cm in length and 5 mm in diameter, surface is glabrous and satiny, color at base 191A, distally one-half developing tinting of N187A. Sepals: 4 fused with exception of apex of each, free portion is triangular in shape 3 mm width and 3 mm in depth with acute apex, 191A in color with a hint of 92B. Corolla features: Papilionaceous (4 segments) with reflexed standard (banner), 2 lateral wings and a concealed keel. Standard (banner): orbicular and strongly reflexed in shape, 1.2 cm in length and 7 mm in width, upper N92D and lower surfaces N89A with mid region having a base of 144B, apex rounded with a single notch, surface is glabrous on all sections. Lateral wings (Alae): lanceolate in shape 1.5 cm in height and 5 mm in width, upper surface and lower surface N92B with a base of 155A, rounded apex and oblique base. Keel: not visible, comprised of 2 segments surrounding reproductive organs, lanceolate in shape with rounded apex and oblique base, 2 cm in length and 7 mm in width, upper and lower surfaces 157A.

*Receptacle.*—disk shaped, gelatinous, N144C in color, 3.5 mm in diameter and 1 mm in depth. Reproductive organs: Gynoecium: 1 pistil 2 cm in length, 1.5 mm in depth; style is 150B in color and 9 mm in length; stigma less than 0.5 mm 150B in color.

*Ovary.*—Superior above hypanthium, suspended by stipe; 6 mm long and 1.5 mm in diameter; color N144C. Style 4 mm long, and 0.5 mm diameter color 144B. Androecium: Stamens ten. Filament: Glabrous; slightly lustrous; not united 10 mm in length, less than 1 mm diameter, slightly curved upward distally; color 157B. Anther: dorsifixed, oblong 1.5 mm long and 1 mm wide; color 17A. Pollen: Spherical; abundant; color 17A.

Fruit:

*Fruit*.—Bivalve inflated ellipsoidal pod; glabrous, 5 cm long and 4 cm across and about 2 mm thick, color starting at N187A and maturing to 200A, numerous seeds per pod (open pollinated), reniform, glabrous, about 4 mm long, 3 mm across, and 2 mm thick, color N199B.

Plant hardiness:

*Plant hardiness*.—USDA Hardiness Zone Map (2012): Zones 4a-9b; heavy clay or light loamy sand soils; able to withstand drought conditions once established.

disease/pest resistance: Susceptibility or resistance to diseases beyond that typically found in other false indigo plants has not been observed.

We claim:

1. A new and distinct *Baptisia* plant named 'PIIBAP-01-21', substantially as illustrated and described herein.

* * * * *